United States Patent
Daners

(10) Patent No.: US 7,203,556 B2
(45) Date of Patent: Apr. 10, 2007

(54) DEVICE FOR MONITORING MEDICAL EQUIPMENT

(75) Inventor: Felix Daners, Schaffhausen (CH)

(73) Assignee: Storz Endoskop Produktions GmbH (DE)

( * ) Notice: Subject to any disclaimer, the term of this patent is extended or adjusted under 35 U.S.C. 154(b) by 146 days.

(21) Appl. No.: 10/971,322

(22) Filed: Oct. 22, 2004

(65) Prior Publication Data

US 2005/0193279 A1    Sep. 1, 2005

Related U.S. Application Data

(63) Continuation of application No. PCT/IB03/03023, filed on Apr. 28, 2003.

(30) Foreign Application Priority Data

Apr. 26, 2002    (DE)    ............... 102 18 894

(51) Int. Cl.
G05B 9/02    (2006.01)
A61B 18/18    (2006.01)
A62B 1/04    (2006.01)
H04N 7/18    (2006.01)

(52) U.S. Cl. ............ 700/79; 331/183; 606/38; 606/40; 348/65

(58) Field of Classification Search ......... 700/79; 714/47; 331/183; 606/38, 40; 348/65
See application file for complete search history.

(56) References Cited

U.S. PATENT DOCUMENTS

| | | | | |
|---|---|---|---|---|
| 4,301,801 A | | 11/1981 | Schneiderman | 128/303.14 |
| 4,818,954 A | * | 4/1989 | Flachenecker et al. | 331/183 |
| 4,860,745 A | * | 8/1989 | Farin et al. | 606/40 |
| 5,108,391 A | * | 4/1992 | Flachenecker et al. | 606/38 |
| 6,791,601 B1 | * | 9/2004 | Chang et al. | 348/65 |

FOREIGN PATENT DOCUMENTS

| | | |
|---|---|---|
| DE | 30 03 891 | 8/1981 |
| DE | 37 36 712 | 5/1988 |
| DE | 39 23 024 | 2/1990 |

* cited by examiner

*Primary Examiner*—Anthony Knight
*Assistant Examiner*—Sunray Chang
(74) *Attorney, Agent, or Firm*—St. Onge Steward Johnston & Reens LLC

(57) ABSTRACT

A medical instrument, in particular a generator for high-frequency surgery, comprises setting elements for presetting functions, and also functional elements for performing functions according to the settings. A controller interrogates the setting elements and controls the functional elements accordingly. Furthermore, a safety controller is provided for performing plausibility checks with the aid of information from the setting elements and also the functional elements, and for deactivating, or putting into a safe operating condition, the functional elements in the case of inadmissible working conditions.

7 Claims, 1 Drawing Sheet

DEVICE FOR MONITORING MEDICAL EQUIPMENT

CROSS REFERENCE TO RELATED APPLICATIONS

This application is a continuation of pending International Application No. PCT/IB03/03023 filed on Apr. 28, 2003, which designated the United States and claims priority from the German Application No. 102 18 894.7 filed on Apr. 26, 2002.

BACKGROUND OF THE INVENTION

The invention relates to a medical instrument, and in particular to a generator for power generation for high-frequency surgery.

1. Field of the Invention

In the case of medical instruments, a matter of foremost concern, apart from that of the actual treatment, is the safety of patients and of persons performing the treatment. Many medical instruments act on a patient by means of electrical or mechanical energy, or require internal electrical or mechanical energy for a performance of their functions. Because of these forms of energy, any faulty handling or malfunction of an instrument may endanger patients or persons performing a treatment. The potential danger will be described by using a high-frequency generator for surgery as an example.

In high-frequency surgery, human or animal body tissue is cut or coagulated by means of an electrical current. High-frequency surgery can be applied with extreme advantage, particularly in combination with endoscopic operating techniques.

It is the object of generators for high-frequency surgery to provide electrical energy for high frequency surgery, so that a desired result of a surgical operation can be achieved. In order to minimize muscle and nerve irritation, generators for high-frequency surgery supply high-frequency energy in a frequency range above 300 kHz. This high frequency energy is usually applied to tissue by means of an electrode. Strong heating of the tissue surrounding the electrode occurs at the point of application. If high energy is applied within a short period of time, this leads to a vaporization of cell fluid and a bursting of cells, so that the group of cells surrounding the electrode is disintegrated. The electrode can move almost freely through the tissue. If less energy is supplied for a long period of time, this leads to a coagulation of the tissue, i.e. to a congealing of protein. In this case, the cells die off and form a viscous mass.

As far as an introduction of high frequency energy is concerned, a basic distinction is made between two arrangements.

In a monopolar arrangement, a cutting or coagulating electrode having a small surface for introducing current is disposed at the site of a surgical operation, and a "neutral" electrode having a large surface for conducting current away is disposed at a different site of the body of a patient. Here the electrode surface is made to be large enough for no appreciable heat to be developed at the electrode.

A bipolar arrangement comprises a divided electrode with which a current is introduced into and a current is conducted away from the site of the operation.

A high-frequency generator can therefore draw considerable amounts of energy from a line, store it internally, and supply it at its output even for a long period of time, for the purpose of cutting or coagulating tissue. High safety demands are made on high-frequency generators for surgery, so that any inadvertent emission of power to the output can be avoided with highest reliability. In the same way, even in a case of a fault occurring for the first time, no higher power should be emitted than that pre-selected by an operator.

2. Description of the Prior Art

Thus, U.S. Pat. No. 6,142,992 provides for a limitation of the power, which automatically limits the emitted power of a generator when the electrode makes no contact with the tissue.

The Patent DE 197 14 972 describes a monitoring of the neutral electrode. This prevents faulty handling when the neutral electrode is applied.

Safety devices known in prior art relate to a monitoring of outer generator functions and to protection from faulty handling. However, protection from internal malfunction of the instrument is just as important as protection from outer faulty handling.

Most of the medical instruments known today are controlled by a central control computer or microprocessor, also known as a controller. Known methods of safety checks, such as interrogation schedules additionally incorporated in the software of the main controller, do not safeguard against a failure of the controller and also not against errors of programming. A multiple redundant arrangement of identical controllers requires a very high outlay of material, and also does not provide a safeguard from programming errors.

BRIEF SUMMARY OF THE INVENTION

The invention is based on the object of providing safety monitoring of medical instruments, in particular of generators for high-frequency surgery, which can detect internal faults and also external operating faults with a high probability, and at the same time is of highest reliability and low cost.

In accordance with the invention, this object is achieved by a medical instrument, in particular a high-frequency generator for high-frequency surgery, comprising: setting elements for presetting values and selecting functions; functional elements for performing the functions as preset by the setting elements and additional fixed preset functions; and at least one main controller for interrogating the setting elements and controlling the functional elements. At least one safety controller is provided for also interrogating the setting elements, and for performing interrogations concerning status information from the functional elements and the controller, and for performing plausibility checks with the obtained information, the safety controller issuing at least one error signal in case of inadmissible conditions, and the error signal deactivating, or putting into a safe working condition, the functional elements.

The device according to the invention comprises a medical instrument, in particular a high-frequency generator for high-frequency surgery, which has setting elements, functional elements, and a main controller for interrogating the setting elements and controlling the functional elements. The setting elements serve for presetting values and selecting functions of the instrument. They comprise all elements which are necessary for setting and controlling instrument functions, such as keyboard keys, switches and also elements for feedback, such as indicators. The functional elements perform the appropriate functions which have been preset by means of the setting elements. The main controller serves as a central communication and control element, and preferably comprises a microcontroller or a programmable logical unit. It is connected to the setting elements and the functional elements by means of suitable signal lines or bus systems.

Furthermore, a safety controller is provided for interrogating the setting elements and also the functional elements, and for performing plausibility checks with the obtained information for the purpose of detecting unacceptable operating conditions or errors. Furthermore, in the case of unacceptable operating conditions or errors, the safety controller issues an error signal which deactivates or puts the functional elements into a safe operating condition. Of course, a plurality of safety controllers may be provided. Thus, various sections of the instrument may be monitored by various controllers. In the same way, it is possible to employ a plurality of controllers in parallel as a redundant system for the same monitoring tasks. Furthermore, a cascaded structure of safety controllers is possible, in which a controller of a succeeding level performs plausibility checks of each of the functions of a controller of a preceding level.

This kind of arrangement in accordance with the invention is substantially safer and more reliable than the known arrangements which have a second main controller. In accordance with the invention, checks are not made by comparison with a redundant system, but in a second, different and independent way. They are performed, for example, with hardware of a completely different kind, together with different software based on different working procedures and basic principles. This substantially reduces systematic errors in hardware and software.

In another embodiment of the invention, setting elements are provided for presetting values and selecting functions exclusively for the purpose of controlling the safety controller. With this separate provision of setting elements, any possibility of the safety controller being affected by other defective component parts, particularly those governed by the main controller, can be excluded. Thus, for example, for the purpose of setting certain particularly critical instrument functions, it is possible to provide simultaneous confirmation by means of two switches or keys. For this, a first key controls the main controller whilst a second key signals an activation of a function to the safety controller. By this means, any unintended performance of an instrument function by an inadvertent actuation of a key is excluded, and at the same time it is possible to avoid defective component parts or componentry from affecting the safety controller.

For the purpose of better illustration, the clearer term "key" will be used instead of the general term "setting element".

Similarly, a single key may be designed to have two separate contact elements for controlling the main controller and the safety controller.

In a further advantageous embodiment of the invention, sampling taps or sensors, connected to functional elements, are provided for transmitting information concerning the instrument status exclusively to the safety controller. With this design, having redundant measurement taps or sensors, even errors caused by faulty sampling taps or sensors that communicate with the main controller can be detected. For example, if a defective output voltage measurement causes an instrument to supply a voltage which is too high, but has been signaled to the main controller as being correct, then a safety controller which uses the same output voltage measurement would also accept the value as being correct. However, by means of an additional output voltage measurement, a safety controller can detect that too high an output voltage is being supplied and thereupon deactivate the instrument.

In a particularly advantageous embodiment of the invention, control elements or circuit elements are provided to enable only the safety controller to deactivate the entire instrument or functional elements, or to affect their working. This can prevent a superposition of different control signals, for example, signals from a defectively functioning main controller with signals from a safety controller that attempts to deactivate the instrument, or to put it into a safe condition.

A further advantageous embodiment of the invention provides a priority circuit for the control elements or circuit elements used in common by the main controller and the safety controller. This priority circuit gives higher priority or precedence to the, or one, safety controller for controlling the control or circuit elements.

A further advantageous embodiment of the invention provides means for signaling an error condition, with the aid of which the safety controller indicates a defective condition, or its intervention with the instrument. Signaling means of this kind may be, for example, an optical indicator element such as a lamp or a luminous diode, means for acoustic signaling, or means for electric signaling making use of control signals or communication via bus systems. Similarly, an indicator may be provided for signaling an error condition and, in particular, further information concerning the error condition using various optical signals such as flashing signals, or even plain language, thus, for example, attention can be drawn to the gravity of an error condition or to failed components or functional elements.

In a further advantageous embodiment of the invention a telecommunication means is provided, with which the safety controller signals an error condition or transmits detailed status information to at least one central unit. By means of such transmission of an error condition, the central unit or a plurality of central units that may possibly be interconnected, may detect and evaluate error conditions. In addition to statistical evaluations concerning instrument reliability and service intervals, a specific control or intervention with a faulty instrument is possible. Thus, for example, a replacement instrument may be activated by the central unit. Similarly, a placement of an order for spare parts, or a demand for service can be made automatically.

BRIEF DESCRIPTION OF THE DRAWINGS

In the following the invention will be described by way of example, without limitation of the general inventive concept, with the aid of embodiments and with reference to the drawings.

DETAILED DESCRIPTION OF THE EMBODIMENTS

Figure 1:
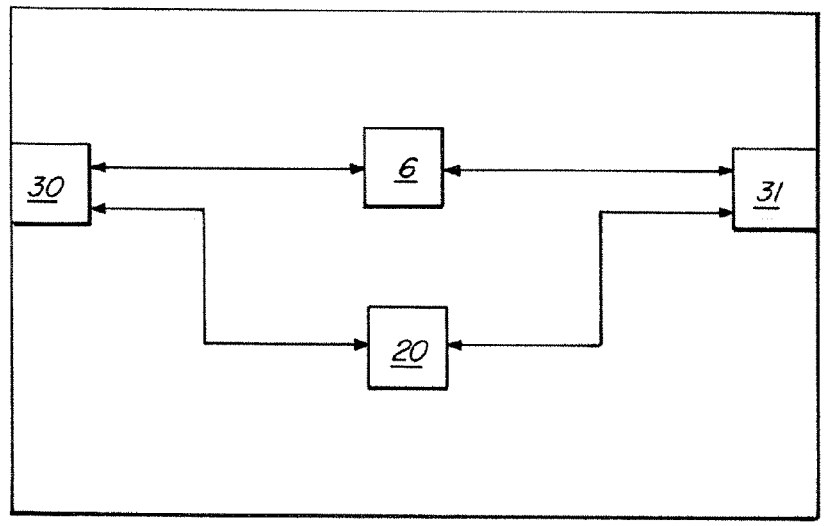
FIG. 1 schematically shows in a general form a device according to the invention.

FIG. 1 schematically shows a device according to the invention. In a medical instrument, operating parameters are preset by means of setting elements 30. Interrogation of these setting elements is effected by a main controller 6 which suitably sets and controls the functional elements 31. Furthermore, a safety controller 20 is present, which also performs an interrogation concerning parameters of the setting elements, and uses these, together with the measured values of the functional elements, to perform a plausibility check. In case of an error, the system is put into a safe operating condition, or is shut-down, by the safety controller. Optionally, the safety controller may operate independently from the main controller, or may ask the main controller for additional information, in particular concerning correct working of the main controller.

Figure 2:
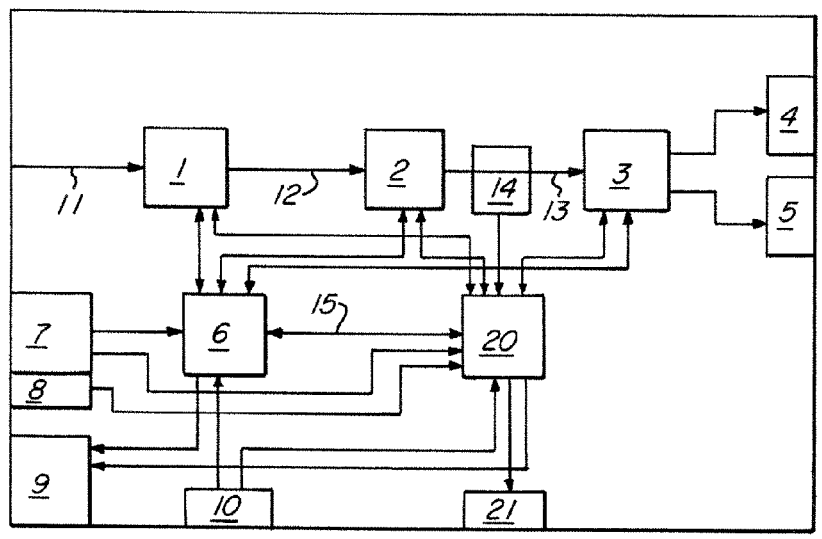
FIG. 2 illustrates the invention using as an example a generator for high-frequency surgery.

FIG. 2 shows the invention clearly for the case of a high-frequency energy generator. A generator for high-frequency surgery comprises a power supply unit 1 for supplying a power generator 2 with an intermediate-circuit voltage 12 from a line voltage 11. The power generator itself supplies a high-frequency voltage 13. A switch matrix 3 provides a connection between the power generator and, for example, a first output socket 4 for connecting a bipolar electrode, and a second output socket 5 for connecting a unipolar electrode and a neutral electrode, according to the desired kind of surgical operation. A main controller 6 controls the functioning of the power supply unit 1, the power generator 2, and the switching matrix 3. It obtains status information from sampling taps on the power supply unit and the power generator. A keyboard 7 serves as setting element for selecting a working mode, or setting generator parameters, the keyboard comprising an additional release key 8 for high-frequency energy. An indicator unit 9 is provided as an operator's facility, or for indicating working conditions. An additional footswitch, adapted to be connected via a footswitch connector 10, additionally serves to activate the generator.

A safety controller 20 monitors input signals of the keyboard 7 in order to ascertain which working mode has been set, or which working parameters have been set. Basically, there are several possibilities of interrogating the keyboard. Modern generators for high-frequency surgery require only very few input elements, so that the keys can be interrogated singly by both the main controller and the safety controller. Similarly, it would be expedient to perform a time-staggered interrogation of the keys by the two controllers. If a keyboard controller is used for keyboard interrogation, then it transmits its output signals to both the main controller and the safety controller. In this case, the safety controller can perform additional safety monitoring, such as, for example, watchdog-timing of the keyboard controller. In the same way, of course, a combined keyboard and indicator controller may be used. From the information on keyboard input, the safety controller can draw conclusions concerning the desired operating condition of the generator. Furthermore, the safety controller may optionally or additionally monitor the indications given by the indicator unit 9, for example in order to perform an interrogation concerning the values of the parameters actually set.

Furthermore, the safety controller obtains information from the functional elements, i.e. the power supply unit 1, the power generator 2 and the switching matrix 3 concerning the operating conditions thereof. As additional safety measures, the safety controller can determine an actual high-frequency voltage of the generator by means of an independent sampling tap 14 for measuring the high-frequency voltage. Furthermore, there is an additional communication line 15 between the safety controller and the main controller. By means of this, the safety controller may obtain further information on operating conditions of the generator and the functioning of the main controller.

The safety controller itself preferably consists of a microcontroller or a programmable logical unit, depending upon the complexity of the generator. Error conditions of the entire system are detected by means of plausibility checks performed in the safety controller. Of course, because the safety controller performs only simple plausibility checks, and is not equipped with all of the functions of the main controller, a plausibility check can be performed only within the scope of the information that is available.

If, for example, a surgical operation of a kind using a constant output voltage is selected, the safety controller checks whether the actually supplied output voltage, or the output voltage indicated by the sampling taps 14, is within given limits of tolerance of the desired output voltage. In the same way, other working modes such as, for example, those involving constancy of current or constancy of power are checked. With more complex working modes, such as those used for making cuts with controlled arcs, or performing coagulations with pulsed signals, the safety controller can monitor the output signal for maintenance of limiting boundary values, such as, for example, those of maximum power or maximum voltage. These limiting boundary values may be preset in dependence upon a selected kind of surgical operation and also a selected intensity (size of arc, depth of coagulation, etc.). Thus, a transmission of these limiting boundary values, as set, may be made from the main controller to the safety controller. However, it is considerably better to provide a memory for setting these limiting boundary values, or a calculation algorithm for calculating the limiting boundary values from the actual settings made, in the safety controller itself.

Monitoring of the actual working conditions is performed independently from maintenance of limiting boundary values. Thus, the power generator may be actuated only after the release key 8 has been operated and the footswitch has been operated at the same time as the generator is activated. An error condition therefore exists when a high-frequency voltage is measured at the generator output without the release key on the keyboard having previously been operated and without the footswitch being operated at the same time as the voltage is supplied. Furthermore, a failure of regular status reports being rendered from the main controller to the safety controller may also be detected as an error condition.

When an error condition is detected, then the safety controller can intervene with the functional elements. Thus, for example, the voltage and current of the power supply unit 1 may be limited, or the unit completely shut down. The power supplied by the power generator 2 may be limited by timing, or the generator may also be completely shut down. The switching matrix 3 may be set so that it interrupts a connection between the power generator 2 and the output sockets 4, 5, so that a safe disconnection from the patient's electrical circuit is achieved. Optionally, some of these measures, or even all measures, may be adopted at the same time.

An indication of error conditions is made, for example, via an error indicator 21 or a display unit 9 for displaying inputs or operating conditions. The error indicator is preferably optical, and in addition to indicating an occurrence of an error, may also give detailed information on the kind of error. This is particularly expedient when a fault may be easily removed by a user. For example, if a neutral electrode is missing or has been wrongly connected, then an indication of this can enable an operating person to remove the fault. In the case of internal errors it is desirable to provide service personnel with concrete indications on causes of an error. Additional acoustic indication may give warning of special errors.

When errors are detected, then steps can be taken according to the fault. Thus, in the case of a simple error, such as may arise from erroneous handling, the generator may be shut down and the display may give an indication to the user. Similarly, in the case of a transient generation of an overvoltage during the performance of a coagulating cut consisting of successive cuts and coagulations, a limitation of the voltage may be made by the safety controller. In the case of serious faults, the generator may be completely shut-down, and in especially serious cases may be put back into working condition only by service personnel.

The actions of the safety controller for bringing the medical instrument into a safe condition may be illustrated particularly simply by using a high-frequency generator for surgery as an example, because in this case a safe condition usually consists of the instrument being shut-down. Particularly in the case of life-supporting systems, it is not acceptable to shut-down the entire system. Here the entire system or a part of the system concerned must be put into a safe operating condition. Conditions of this kind are basically also conceivable in the case of high-frequency generators for surgery. If, for example, the generator is completely shut-down for reasons of safety exactly at a time when a large blood vessel is being coagulated, this can lead to a strong and dangerous bleeding of the patient. For cases of this kind, a manual emergency working condition of the generator may be provided to make it possible to complete the surgical operation. A condition for this is, of course, that the entire high-frequency power path still functions correctly. Thus, this emergency working condition could still be made use of, for example, during a failure of arc regulation, or of one or more of the components needed for this, such as, for example, a distortion factor detector.

Furthermore, it is of advantage to provide a memory for storing error conditions in the safety controller. Thus, information on the kind and boundary conditions of the errors may be read out from this memory at a later time. It is particularly expedient to design this memory, or at least a part of the memory, to be an interchangeable medium, e.g. a memory card, so that it can be easily evaluated with a suitable evaluating instrument.

List of Reference Symbols
1 power supply unit
2 power generator
3 switching matrix
4 first output socket
5 second output socket
6 main controller
7 keyboard
8 release key
9 display unit
10 footswitch connector
11 line voltage
12 intermediate-circuit voltage
13 high-frequency voltage
14 sampling taps
15 communication line
20 safety controller
21 error indicator
30 setting elements
31 functional elements

What is claimed is:

1. Medical instrument, in particular a high-frequency generator for high-frequency surgery, comprising:
   setting elements for presetting values and selecting functions,
   functional elements for performing functions as preset by the setting elements, and additional fixed preset functions, and
   at least one main controller for interrogating the setting elements and controlling the functional elements;
   wherein at least one safety controller for detecting internal faults of the instrument and also external operating faults is provided;
said safety controller interrogating the setting elements, and performing interrogations concerning status information from said functional elements and said main controller, and performing plausibility checks with obtained information; and
said safety controller issuing at least one error signal in case of inadmissible conditions, and an error signal deactivating, or putting into a safe working condition, said functional elements.

2. Medical instrument according to claim 1, wherein setting elements for presetting values and selecting functions are connected exclusively to the safety controller.

3. Medical instrument according to claim 1, wherein sampling taps or sensors, connected to functional elements, are provided for transmitting information concerning instrument status exclusively to the safety controller.

4. Medical instrument according to claim 1, wherein control elements or circuit elements are provided which are exclusively controlled by the safety controller, and which can deactivate, or affect working of, the entire instrument or functional elements.

5. Medical instrument according to claim 1, wherein control elements or circuit elements which are controlled jointly by the main controller and the safety controller comprise a priority circuit that assigns a higher priority of control to the safety controller.

6. Medical instrument according to claim 1, wherein means for signaling are provided, with which the safety controller indicates an error condition or its intervention with the instrument.

7. Medical instrument according to claim 1, wherein means for telecommunication with a central unit disposed at a distance from the medical instrument are provided for signaling an error condition to the central unit, and optionally transmitting detailed status information and also additional control information or control interrogations from or to the central unit.

* * * * *